US006068832A

United States Patent [19]
Berry et al.

[11] Patent Number: 6,068,832
[45] Date of Patent: May 30, 2000

[54] CHLOROFLUOROCARBON-FREE MOMETASONE FUROATE AEROSOL FORMULATIONS

[75] Inventors: Julianne Berry, Westfield; Joel A. Sequeira, Edison; Imtiaz A. Chaudry, North Caldwell, all of N.J.

[73] Assignee: Schering Corporation, Kenilworth, N.J.

[21] Appl. No.: 08/920,611

[22] Filed: Aug. 27, 1997

Related U.S. Application Data

[60] Provisional application No. 60/025,807, Aug. 29, 1996.
[51] Int. Cl.$^7$ ...................................................... A61K 9/12
[52] U.S. Cl. .................................................. 424/45; 424/46
[58] Field of Search ........................................ 424/45, 46

[56] References Cited

U.S. PATENT DOCUMENTS

| | | |
|---|---|---|
| 5,118,494 | 6/1992 | Schultz et al. .............................. 424/45 |
| 5,225,183 | 7/1993 | Purewal et al. . |
| 5,474,759 | 12/1995 | Fassberg et al. ........................... 424/45 |
| 5,653,962 | 8/1997 | Akehurst et al. .......................... 424/45 |
| 5,658,549 | 8/1997 | Akehurst et al. .......................... 424/45 |
| 5,674,471 | 10/1997 | Akehurst et al. ......................... 424/45 |

FOREIGN PATENT DOCUMENTS

| | | |
|---|---|---|
| 0 656 205 | 6/1995 | European Pat. Off. . |
| 92/06675 | 4/1992 | WIPO . |
| 93/11745 | 6/1993 | WIPO . |
| 94/03153 | 2/1994 | WIPO . |
| 95/20393 | 8/1995 | WIPO . |

*Primary Examiner*—Raj Bawa
*Attorney, Agent, or Firm*—Robert A. Franks

[57] ABSTRACT

The invention relates to suspension aerosol formulations which exhibit stable particle sizes, containing mometasone furoate, about 1 to about 10 weight percent ethanol and 1,1,1,2,3,3,3-Heptafluoropropane as the propellant. A surfactant, such as oleic acid, can also be included. These formulations are suitable for use in metered dose inhalers.

18 Claims, No Drawings

CHLOROFLUOROCARBON-FREE MOMETASONE FUROATE AEROSOL FORMULATIONS

This application claims benefit of provisional application Ser. No. 60/025,807 filed Aug. 29, 1996.

INTRODUCTION TO THE INVENTION

The present invention pertains to aerosol formulations of drugs, such as those formulations suitable for use in pressurized aerosol metered dose inhalers. More specifically, the invention relates to aerosol formulations of the drug mometasone furoate with the propellant 1,1,1,2,3,3,3-Heptafluoropropane (HFC-227).

Aerosolized drugs have been used for many years to treat disorders of the respiratory system, and as a convenient means for the systemic introduction of various pharmaceutical agents into the body. The typical aerosol formulation in a metered dose inhaler for treating disorders such as asthma or rhinitis is a suspension of one or more drug substances in a fully halogenated (with chlorine and fluorine) lower alkyl compound propellant, further containing small amounts of surfactants and/or excipients which are usually soluble in the propellant.

Pharmaceutical agents administered by means of metered dose inhalers are usually bronchodilators or corticosteroids. The steroidal drugs which are currently available in this form for inhalation therapeutic uses in the United States include beclomethasone dipropionate (both for nasal and lower airway administration), budesonide (nasal and airway administration), dexamethasone sodium phosphate (nasal and airway administration), flunisolide (nasally administered), and triamcinolone acetonide (nasal and airway administration). Fluticasone propionate has also recently been approved for sale as a lower airway drug. Typical formulations contain chlorofluorocarbon propellants, the drug substance and ethanol, which is soluble in the propellant, and sometimes also contain a surfactant such as oleic acid for maintaining a stable suspension, lubrication of the metering valve and other functions.

However, certain of the steroids have significant solubility in ethanol. When there is insufficient ethanol present for maintaining a solution of these drugs in an aerosol canister, the normal temperature fluctuations encountered during storage and use can cause repeated solubility increases and decreases of a saturated solution. Each time the drug substance becomes less soluble, such as in a period of ambient temperature decrease, it tends to crystallize and, due to the typical slow rate of temperature change, grows into crystals much larger than those which can be properly dispensed—particularly when the drug is intended for delivery to the bronchia or lungs. In general, drug particle sizes from about 1 to about 5 micrometers are preferred for administration to the lower airway, with particles smaller than about 0.5 micrometers frequently being exhaled without complete deposition on tissues, while particles larger than about 10 micrometers can exhibit considerable deposition in the mouth and/or pharynx and therefore not reach the lower airway. Very large particles cannot pass through a metering valve and will not be reliably dispensed.

In the case of beclomethasone dipropionate, itself quite soluble in ethanol, an addition compound (sometimes called a "solvate" or "clathrate") can be formed from the compound and the chlorofluorocarbons or a fluorohydrocarbon; when this clathrate is formulated with a propellant, no particle size growth is noted.

With the implication of fully halogenated chlorofluorocarbon propellants in the environmentally harmful destruction of ozone in the upper atmosphere, the availability of these propellants has become quite restricted. This has encouraged development work toward formulations containing propellants having reduced upper atmospheric reactivity, such work particularly centering about the propellants 1,1,1,2-Tetrafluoroethane (HFC-134a) and HFC-227, these compounds having approximately the same physical properties as those of the older chlorofluorocarbons used for medicinal aerosols. Recent studies have imputed to HFC-134a an undesirable potential for surface water acidification, as it appears to form the environmentally very stable trifluoroacteic acid in the atmosphere.

It has been proposed in European Patent 0 553 298 B1 to formulate an aerosol with HFC-134a by simply including sufficient ethanol to maintain beclomethasone dipropionate in solution over at least the expected ambient temperature range. However, the presence of any ethanol is discouraged in many countries, due to the prevalence of alcoholism and the ease with which ethanol is systemically absorbed from lower airway tissues. Any products intended for use by children generally should have as low an ethanol content as possible.

International Patent Application WO 93/11745 discloses particle size-stable suspension aerosol formulations containing drug substances, a fluorocarbon or hydrogen-containing chlorofluorocarbon propellant, and a polar cosolvent such as an alcohol. No surfactants are said to be required.

International Patent Application WO 94/03153 reports that solvates of beclomethasone and HFC-134a can be used to produce stable suspensions in a fluorocarbon or hydrogen-containing chlorofluorocarbon propellant, in the substantial absence of solvating species such as alcohol.

The drug mometasone furoate would have advantages over the presently available corticosteroids for treating airway disorders. As reported in International Patent Application WO 95/20393, the drug has a very rapid onset of action and generally does not appear in detectable concentrations in the blood, following nasal or airway administration.

Unfortunately, this drug has some solubility in ethanol and exhibits particle size increases during storage of suspension aerosol formulations prepared using large amounts of ethanol.

International Patent Applications WO 92/22287 and WO 92/22288 disclose aerosol formulations of mometasone furoate in the propellants HFC-134a and HFC-227, but do not address the problem of adverse particle size increases.

SUMMARY OF THE INVENTION

In accordance with the invention, there is provided a particle size-stable pressurized aerosol suspension formulation of mometasone furoate, comprising the propellant HFC-227, about 1 to about 10 weight percent ethanol and mometasone furoate in concentrations at least about 1 percent of the ethanol concentration. The formulation can also contain a surfactant.

It has been discovered that the formulation of the invention does not exhibit significant particle size changes in the suspended drug. In addition, the densities of the solid and liquid phases are similar, giving a suspension which has a reduced tendency for particle settling; this results in a greatly facilitated re-dispersion into a uniform suspension, after the formulation has remained in an undisturbed condition for prolonged periods.

DETAILED DESCRIPTION OF THE INVENTION

The invention provides pressurized aerosol formulations of the corticosteroid drug mometasone furoate, particularly formulations suitable for use in metered dose inhalers.

Mometasone furoate is also known by the chemical name 9α,21-Dichloro-11β,17-dihydroxy-16α-methylpregna-1,4-diene-3,20-dione 17-(2-furoate), has the empirical formula $C_{27}H_{30}Cl_2O_6$ and has a molecular weight of 521.44. The drug is currently marketed in cream, ointment and lotion formulations, for the treatment of various dermatological conditions.

In formulations of the present invention which are suitable for treating lower respiratory system disorders such as asthma, at least a substantial portion of the drug is present as suspended particles having respirable sizes, e.g., about 0.5 to about 10 micrometers in their largest dimension. In inventive formulations which are suitable for treating upper respiratory system disorders such as rhinitis, somewhat larger drug particles may be permissible, but the foregoing size range remains preferred.

As with other drugs which have appreciable solubility in ethanol, there is a tendency for mometasone furoate to exhibit crystal growth in ethanol-containing formulations. However, the inventors have discovered formulation parameters which do not promote drug particle size growth. These parameters also provide the advantage of minimizing the required ethanol concentrations, to reduce the potential for unpleasant taste sensations and render the compositions more suitable for use by children and others with low alcohol tolerance.

It has been discovered that a certain minimum level of ethanol is needed to provide consistent and predictable delivery of the drug from a metered dose dispenser. This minimum level is about 1 weight percent of the total formulation, which results in a marginally acceptable drug delivery. Increased amounts of ethanol generally improve drug delivery characteristics.

However, for reasons previously discussed, and to prevent drug crystal growth in the formulation, it is necessary to limit the concentration of ethanol. Experimental data indicate that the ratio of the weight of mometasone furoate to the weight of ethanol is important in preventing particle size increases; in general, when the drug is present at 0.6 percent of the concentration of ethanol, immediate and severe adverse changes in crystal morphology and size are observed. This effect is not seen when the mometasone furoate is present at 1.3 percent of the ethanol concentration, leading to a conclusion that the drug must be present in concentrations at least about 1 percent of the ethanol concentration.

Limitations in the available metering valve delivery volumes (e.g., 25 to 100 microliters per actuation) and the amounts of drug substance required in a dose for treating a particular condition (generally about 10 to about 500 micrograms per valve actuation) will dictate the points within the foregoing ethanol parameters for a given formulation. Determination of such amounts is well within the skill of workers in this art.

A surfactant is frequently included in aerosol formulations, for purposes such as assisting with maintaining a stable suspension of the drug and lubricating the metering valve. The formulation of the present invention does not require a surfactant for maintenance of ready dispersability (such as by moderate agitation immediately prior to use), as the drug forms loose flocculates in the propellant and does not exhibit a tendency to settle or compact. Upon undisturbed storage, the drug particles merely remain in their flocculated state.

However, surfactants can be incorporated, in small amounts as are customary in other aerosol suspensions, to ensure proper metering valve function. The commonly used oleic acid is suitable, at levels which will deliver up to about 50 micrograms of oleic acid per actuation of the valve. Of course, it is always desired to minimize the amounts of chemical substances in a medication dose, so the lowest concentrations which yield the desired effects are to be used. Other useful surfactants include, without limitation thereto, sorbitan trioleate, cetyl pyridinium chloride, soya lecithin, polyoxyethylene (20) sorbitan monolaurate, polyoxyethylene (10) stearyl ether, polyoxyethylene (2) oleyl ether, polyoxyethylene-polyoxypropylene-ethylenediamine block copolymers, polyoxyethylene (20) sorbitan monostearate, polyoxyethylene-polyoxypropylene block copolymers, castor oil ethoxylate, and mixtures of any of the surfactants. It is generally preferred that the surfactant is soluble, at levels employed, in the alcohol-propellant solution. For any desired surfactant, simple experiments to measure drug delivery reproducibility can be employed to identify the optimum amount of surfactant for any given formulation and delivery system.

Formulations of the invention are made according to procedures customary in the art for other aerosol compositions. Typically, all components except the propellant are mixed and introduced into aerosol containers. The containers can then be chilled to temperatures below the boiling point of the propellant, and the required amount of the chilled propellant added before the metering valve is crimped onto the container. Alternatively, the containers can be fitted with a metering valve before being filled with propellant, and the required quantity of propellant will be introduced through the valve.

Certain aspects of the invention are further described in the following examples. In the examples, "percent" indicates weight percentage unless the context clearly indicates otherwise.

EXAMPLE 1

Following are examples of useful aerosol suspension formulations, according to the present invention. Ingredient amounts, in percent of mometasone furoate ("MF"), oleic acid ("Oleic"), ethanol ("EtOH") and HFC-227 ("Propellant"), are given.

| Formulation | MF | Oleic | EtOH | Propellant |
|---|---|---|---|---|
| A | 0.112 | 0.001 | 2.497 | 97.389 |
| B | 0.028 | 0 | 1.750 | 98.222 |
| C | 0.112 | 0.011 | 2.497 | 97.379 |
| D | 0.448 | 0.011 | 2.489 | 97.052 |
| E | 0.112 | 0 | 2.497 | 97.390 |
| F | 0.448 | 0.011 | 4.977 | 94.564 |
| G | 0.224 | 0.011 | 2.494 | 97.270 |
| H | 0.028 | 0.001 | 2.499 | 97.471 |
| I | 0.028 | 0.011 | 2.499 | 97.462 |

EXAMPLE 2

Experiments are performed to determine the effects on aerosol drug delivery characteristics from variable, low concentrations of ethanol. In these experiments, micronized mometasone furoate is incorporated into a "concentrate" suspension with the ethanol and, optionally, oleic acid. A required amount of the well-mixed concentrate for delivery of 120 doses is weighed into metal aerosol containers, a metering valve delivering 63 microliters per actuation (a volume containing 100 micrograms of mometasone furoate)

is crimped onto the container and liquid HFC-227 propellant is weighed into the container through the valve. The concentration of mometasone furoate in the final formulation is 0.112%.

To test drug delivery from the containers, the weight of drug substance delivered by two actuations of the metering valve is measured, and divided by two to calculate the amount delivered in a single actuation. After a fixed number of "priming" actuations, this is done for the first two doses delivered from the container, two doses at the midpoint of doses to be delivered and two doses at the end of the intended capacity of the container. Tabulated below are average amounts recovered from multiple containers of each formulation, the formulation information identifying the amount of oleic acid delivered with each valve actuation.

| 1% Ethanol, 2.5 µg Oleic Acid (6 containers) | |
|---|---|
| Beginning | 75.2 µg |
| Midpoint | 83.4 µg |
| End | 92.6 µg |
| 1.75% Ethanol, 10 µg Oleic Acid (6 containers) | |
| Beginning | 94.3 µg |
| Midpoint | 96.4 µg |
| End | 110 µg |
| 2.5% Ethanol, 10 µg Oleic Acid (10 containers) | |
| Beginning | 104 µg |
| Midpoint | 102 µg |
| End | 106 µg |
| 2.5% Ethanol, no Oleic Acid (10 containers) | |
| Beginning | 93.3 µg |
| Midpoint | 98.8 µg |
| End | 99.0 µg |

The drug delivery from those containers having 1 percent ethanol could be marginally acceptable for a commercial product, while deliveries from all of the containers with higher alcohol level formulations would be acceptable. The general drug delivery standards for inhalation products intended to treat asthma are established by governmental agencies, such as the United States Food and Drug Administration.

EXAMPLE 3

Experiments are conducted to determine the effects on drug particle size stability of variable ratios of drug to ethanol weights in aerosol formulations.

Formulations are prepared in glass containers, fitted with aerosol valves, from the following components, where amounts are in percent:

| Formulation A | |
|---|---|
| HFC-227 | 94.969 |
| Ethanol | 4.985 |
| Mometasone Furoate | 0.034 |
| Oleic Acid | 0.012 |
| Mometasone Furoate/Ethanol = 0.00674 | |
| Formulation B | |
| HFC-227 | 97.457 |
| Ethanol | 2.499 |
| Mometasone Furoate | 0.032 |
| Oleic Acid | 0.011 |

| -continued | |
|---|---|
| Mometasone Furoate/Ethanol = 0.0130 | |
| Formulation C | |
| HFC-227 | 97.366 |
| Ethanol | 2.497 |
| Mometasone Furoate | 0.127 |
| Oleic Acid | 0.011 |
| Mometasone Furoate/Ethanol = 0.0508 | |
| Formulation D | |
| HFC-227 | 97.188 |
| Ethanol | 2.492 |
| Mometasone Furoate | 0.308 |
| Oleic Acid | 0.011 |
| Mometasone Furoate/Ethanol = 0.124 | |

Each formulation is examined for evidence of crystal growth after preparation, by visually inspecting the container contents and by spraying a dose of the formulation onto a glass microscope slide, allowing the propellant to evaporate and visually inspecting particles on the slide with polarized light at 100X magnification. Formulation A shows extensive crystal morphology change, into elongated needle-like shapes, of which many have a maximum dimension appearing to be greater than about 30 µm; the changes are visually apparent in the container without any magnification. Particles in each of the other formulations appear similar to those of the original micronized mometasone furoate, both in particle form and in size. Formulation A will not be suitable for the inhalation delivery of mometasone furoate.

The containers with Formulations B, C and D are subjected to a freeze/thaw temperature program, as follows: −20° C. for 3 days, then room temperature for one day, then 50° C. for 2 days, then −20° C. for 4 days, then 50° C. for 3 days, then −20° C. for 3 days, then 50° C. for 3 days, and finally room temperature for 1 day. Upon repeating the microscopic examination, no temperature excursion-induced changes in particle form or size are observed in any of these formulations.

The foregoing descriptions of various embodiments of the invention are representative of various aspects of the invention, and are not intended to be exhaustive or limiting to the precise forms disclosed. Many modifications and variations undoubtedly will occur to those having skill in the art. It is intended that the scope of the invention shall be fully defined solely by the appended claims.

What is claimed is:

1. An aerosol suspension formulation comprising 1,1,1,2,3,3,3-Heptafluoropropane, about 1 to about 10 weight percent ethanol and micronized mometasone furoate in concentrations at least about 1 percent of the ethanol concentration, the formulation optionally also containing a surfactant.

2. The aerosol suspension formulation of claim 1, comprising about 1 to about 5 weight percent ethanol.

3. The aerosol suspension formulation of claim 1, comprising about 2 to about 5 weight percent ethanol.

4. The aerosol suspension formulation of claim 1, which contains a surfactant.

5. The aerosol suspension formulation of claim 4, wherein the surfactant comprises oleic acid.

6. The aerosol suspension formulation of claim 1, which is contained in a metered dose container.

7. The aerosol suspension formulation of claim 1, which is contained in apparatus delivering a measured amount of about 10 to about 500 micrograms of mometasone furoate from a single actuating operation.

8. A method for treating allergic reactions in the respiratory tract, comprising administering by inhalation an aerosol suspension formulation comprising 1,1,1,2,3,3,3-Heptafluoropropane, about 1 to about 10 weight percent ethanol and micronized mometasone furoate in concentrations at least about 1 percent of the ethanol concentration, the formulation optionally also containing a surfactant.

9. The method of claim 8, wherein the suspension comprises about 1 to about 5 weight percent ethanol.

10. The method of claim 8, wherein the suspension comprises about 2 to about 5 weight percent ethanol.

11. The method of claim 8, wherein the suspension contains a surfactant.

12. The method of claim 11, wherein the surfactant comprises oleic acid.

13. The method of claim 8, wherein the suspension is contained in a metered dose container.

14. The method of claim 8, wherein the suspension is contained in apparatus delivering a measured amount of about 10 to about 500 micrograms of mometasone furoate from a single actuating operation.

15. A metered dose inhaler which contains an aerosol suspension formulation comprising 1,1,1,2,3,3,3-Heptafluoropropane, about 1 to about 10 weight percent ethanol and micronized mometasone furoate in concentrations at least about 1 percent of the ethanol concentration, the formulation optionally also containing a surfactant.

16. The metered dose inhaler of claim 15, wherein about 10 to about 500 micrograms of mometasone furoate are delivered from a single actuating operation.

17. The metered dose inhaler of claim 15, which is adapted for nasal delivery of mometasone furoate.

18. The metered dose inhaler of claim 15, which is adapted for lower airway delivery of mometasone furoate.

* * * * *